(12) United States Patent
Kaplan

(10) Patent No.: US 7,282,020 B2
(45) Date of Patent: Oct. 16, 2007

(54) DEFLECTABLE IMPLANTATION DEVICE AND METHOD OF USE

(75) Inventor: Edward J. Kaplan, Boca Raton, FL (US)

(73) Assignee: Microspherix LLC, Boca Raton, FL (US)

( * ) Notice: Subject to any disclaimer, the term of this patent is extended or adjusted under 35 U.S.C. 154(b) by 685 days.

(21) Appl. No.: 10/127,107

(22) Filed: Apr. 22, 2002

(65) Prior Publication Data

US 2002/0173689 A1 Nov. 21, 2002

Related U.S. Application Data

(60) Provisional application No. 60/285,959, filed on Apr. 24, 2001, provisional application No. 60/301,031, filed on Jun. 26, 2001.

(51) Int. Cl.
A61M 36/00 (2006.01)
A61N 5/00 (2006.01)

(52) U.S. Cl. .......................................................... 600/7

(58) Field of Classification Search ................ 600/1–8, 600/29, 30, 32; 604/19–22, 53, 99–102, 604/113, 115, 116, 138, 156, 272, 164; 601/2; 606/130, 108
See application file for complete search history.

(56) References Cited

U.S. PATENT DOCUMENTS

| | | | |
|---|---|---|---|
| 2,269,963 A | 1/1942 | Wappler | |
| 4,027,668 A * | 6/1977 | Dunn | 604/180 |
| 4,616,656 A | 10/1986 | Nicholson et al. | |
| 4,700,692 A | 10/1987 | Baumgartner | |
| 4,799,495 A | 1/1989 | Hawkins et al. | |
| 4,926,860 A | 5/1990 | Stice et al. | |
| 5,000,912 A | 3/1991 | Bendel et al. | |
| 5,011,473 A | 4/1991 | Gatturna | |
| 5,219,358 A | 6/1993 | Bendel et al. | |
| 5,242,373 A | 9/1993 | Scott et al. | |
| 5,486,161 A * | 1/1996 | Lax et al. | 604/22 |
| 5,741,225 A * | 4/1998 | Lax et al. | 604/22 |
| 5,788,713 A * | 8/1998 | Dubach et al. | 606/130 |
| 5,860,909 A | 1/1999 | Mick et al. | |
| 5,928,130 A | 7/1999 | Schmidt | |
| 5,938,583 A | 8/1999 | Grimm | |

(Continued)

FOREIGN PATENT DOCUMENTS

WO WO96/14800 5/1996

(Continued)

OTHER PUBLICATIONS

Watson, "Ultrasound anatomy for prostate brachytherapy," *Seminars in Surgical Oncology* 13: 391-398 (1997).

(Continued)

*Primary Examiner*—Samuel G. Gilbert
(74) *Attorney, Agent, or Firm*—Pabst Patent Group LLP

(57) ABSTRACT

Systems, apparatus, components and methods are disclosed that allow the clinician to circumvent the pubic arch in instances where it interferes with insertion of instrumentation into the prostate or periprostatic tissue. The systems, apparatus and components disclosed herein employ structures, such as needles and trocars, of shape memory alloys, such as nickel-titanium (Ni—Ti) for the purpose of avoiding the pubic arch when accessing the prostate from the perineum.

14 Claims, 8 Drawing Sheets

U.S. PATENT DOCUMENTS

| | | | |
|---|---|---|---|
| 6,007,474 A | 12/1999 | Rydell | |
| 6,027,446 A | 2/2000 | Pathak et al. | |
| 6,033,404 A | 3/2000 | Melzer et al. | |
| 6,129,670 A | 10/2000 | Burdette et al. | |
| 6,200,255 B1 | 3/2001 | Yu | |
| 6,210,315 B1 | 4/2001 | Andrews et al. | |
| 6,246,898 B1 | 6/2001 | Vesely et al. | |
| 6,311,084 B1 | 10/2001 | Cormack et al. | |
| 6,368,331 B1 | 4/2002 | Front et al. | |
| 6,402,677 B1 | 6/2002 | Jacobs | |
| 6,482,178 B1 | 11/2002 | Andrews et al. | |
| 6,572,593 B1 * | 6/2003 | Daum | 604/264 |
| 6,572,608 B1 | 6/2003 | Lee et al. | |
| 2001/0041835 A1 | 11/2001 | Front et al. | |
| 2001/0041838 A1 | 11/2001 | Holupka et al. | |
| 2002/0077687 A1 | 6/2002 | Ahn | |
| 2003/0032929 A1 * | 2/2003 | McGuckin, Jr. | 604/272 |

FOREIGN PATENT DOCUMENTS

| | | | |
|---|---|---|---|
| WO | WO98/01179 | 1/1998 | |
| WO | WO 00/33909 | * 6/2000 | 604/272 |

OTHER PUBLICATIONS

Zelefsky, et al., "Intraoperative conformal optimization for transperineal prostate implantation using magnetic resonance spectroscopic imaging," *Cancer J.* 6(4) 249-255 (2000).

Bellon, et al., "Use of pelvic CT scanning to evaluate pubic arch interference of transperineal prostate brachytherapy," *Int J Radial Oncol Biol Phys* 43(3):579-81 (1999).

Blasko, et al., "Brachytherapy for Carcinoma of the Prostate: Techniques, Patient Selection, and Clinical Outcomes," *Seminars in Radiation Oncology* 12(1): 81-94 (2002).

Cormack, et al., "Optimizing target coverage by dosimetric feedback during prostate brachytherapy," *Int J. Radiation Oncology Biol. Phys.* 48(4): 1245-1249 (2000).

Dawson, et al., "Dose effects of seeds placement deviations from pre-planned positions in ultrasound guided prostate implants," *Radiotherapy and Oncology* 32: 268-270 (1994).

Duerig, "The use of superelasticity in modern medicine," *Materials Research Society* 27(2): 101-104 (2002).

Fichtinger, et al., "System for robotically assisted prostate biopsy and therapy with intraoperative CT guidance," *Academic Radiology* 9(1): 60-74 (2002).

Frank, et al., "Instruments based on shape-memory alloy properties for minimal access surgery, interventional radiology and flexible endoscopy," *Min Invas Ther & Allied Technol* 9(2): 89-98 (2000).

Garzotto, et al., "Historical perspective on prostate brachytherapy," *J. Endourology* 14(4): 315-318 (2000).

Grado, "Techniques to achieve optimal seed placement in salvage and primary brachyterhapy for prostate cancer," *Techniques in Urology* 6(2): 157-165 (2000).

Holm, et al., "Transperineal 125iodine seed implantation in prostatic cancer guided by transrectal ultrasonography," *J Urol* 130(2):283-286 (1983).

Holm, "The history of interstitial brachytherapy of prostatic cancer," *Seminars in Surgical Oncology* 13: 431-437 (1997).

Kooy, et al., "A software system for interventional magnetic resonance image-guided prostate brachytherapy," *Computer Aided Surgery* 5: 401-413 (2000).

Lamb, et al., "Analysis of prostate seed loading for permanent implants," *J. of Endourology* 14(4): 337-341 (2000).

Moorleghem, et al., "Shape memory and superelastic alloys: the new medical materials with growing demand," *Bio-Medical Materials & Engineering* 8: 55-60 (1998).

Nag, et al., "American Brachytherapy Society Survey of Current Clinical Practice for Permanent Brachytherapy of Prostate Cancer," *Brachyther Int* 13:243-251 (1997).

Nag, et al., "American Brachytherapy Society (ABS) recommendations for transperineal permanent brachytherapy of prostate cancer," *Int J Radiat Oncol Biol Phys* 44(4):789-799 (1999).

Nag, et al., "Intraoperative planning and evaluation of permanent prostate brachytherapy: report of the American Brachytherapy Society," *Int. J. Radiation Oncology Biol. Phys.* 51(5): 1422-1430 (2001).

Otsuka, et al., "Science and technology of shape-memory alloys: new developments," *Materials Research Society* 27(2): 91-98 (2002).

Pathak, et al., "Pubic arch detection in transrectal ultrasound guided prostate cancer therapy," *IEEE Transactions on Medical Imaging* 175(5): 762-771 (1998).

Peschel, et al., "Pubic arch interference in permanent prostate implant patients," *J Brachyther Intl* 14:241-248 (1998).

Popowski, et al., "Open magnetic resonance imaging using titanium-zirconium needles: improved accuracy for interstitial brachytherapy implant?" *Int. J. Radiation Oncology Biol. Phys.* 47(3): 759-765 (2000).

Stoeckel, "Nitinol medical devices and implants," *Min Invas Ther & Allied Technol* 9(2): 81-88 (2000).

Stone, et al., "Prostate brachytherapy in patients with prostate volumes >= 50 $cm^3$: Dosimetric Analysis of Implant Quality," *Int. J. Radiation Oncology Biol. Phys.* 46(5): 1199-1204 (2000).

Strang, et al., "Real-Time US versus CT Determination of Pubic Arch Interference for Brachytherapy," *Radiology* 387-393 (2001).

Tincher, et al., "Effects of pelvic rotation and needle angle on public arch interference during transperineal prostate implants," *Int. J. Radiation Oncology Biol. Phys.* 47(2): 361-363 (2000).

Wallner, et al., *Prostate Brachytherapy Made Complicated*, pp. 8.24-8.31, SmartMedicine Press: Seattle, 2001.

Wallner, et al., "An improved method for computerized tomography-planned transperineal 125iodine prostate implants," *J. Urol.* 146(1):90-5 (1991).

Wallner, et al., "Use of trus to predict pubic arch interference of prostate brachytherapy," *Int. J. Radiation Oncology Biol. Phys* 43(3): 583-585 (1999).

Wang, et al., "Transperineal brachytherapy in patients with large prostate glands," *Int. J. Cancer* 90: 199-205 (2000).

* cited by examiner

DEFLECTABLE IMPLANTATION DEVICE AND METHOD OF USE

CROSS-REFERENCES TO RELATED APPLICATIONS

This application claims priority from and is related to U.S. Provisional Patent Applications, Ser. Nos. 60/285,959, filed Apr. 24, 2001, entitled: Deflectable Implantation Device And Method For Use, and 60/301,031, filed Jun. 26, 2001, entitled: Deflectable Trocar with Cannula And Stylet For Brachytherapy And Method For Use, both of these provisional applications incorporated by reference herein.

TECHNICAL FIELD

This disclosure relates to a medical device for implantation of treatment elements, such as radioactive seeds and spacers, into living tissue. Specifically, it relates to shape-memory instruments, such as needles and trocars, that allow users to bypass obstructions in the instrument's path.

BACKGROUND

Since 1983, when Holm published his technique for transperineal interstitial implantation of radioactive seeds into the prostate (J Urol 1983; 130:283-6), prostate brachytherapy has grown into an industry. Selected prostate cancer patients are now routinely counseled regarding brachytherapy as a treatment option. By virtue of the fact that more than 30% of newly diagnosed cancers in men arise in the prostate, prostate brachytherapy has become an important procedure. Certain technical aspects of the procedure, such as radiation dosimetry and ultrasound technology, have improved and/or are better understood than in 1983. However, the implant needles upon which physicians rely to deliver radiation to the prostate have not kept pace. This is because devices and techniques are unable to overcome pubic arch interference, the most common problem facing the prostate brachytherapist.

As shown in FIG. 1, a substantial portion of the prostate gland 10, typically the anterolateral portion of the prostate 10a, shown by the x's, (from the clinician's perspective, looking towards the supine patient's head from below), may sit behind the pubic arch 11. This pubic arch 11 is formed by the convergence of the right 12 and left 13 pubic bones at the midline. This pubic arch 11 is closer to the perineum 14, than the prostate 10. The rectum 15 is located posteriorly.

Standard prostate brachytherapy is performed with the patient supine in the lithotomy position. As shown in FIG. 2A, the patient's legs (not shown) are suspended in stirrups. A needle 16 is employed, and a rectangular template (template grid) or needle guide 17 is placed against the perineum 14. The needle guide 17 rests on a support, which holds an ultrasound probe (not shown) that is inserted into the rectum 15. This ultrasound probe permits visualization of the prostate 10 during the procedure. The ultrasound support, in turn, rests on a stand or brace that is locked in place during the actual implant so that the ultrasound probe can be moved forward and back in relation to a defined position in space.

The needle guide 17 has a parallel array of holes extending therethrough, for accommodating the needle 16. These holes are perpendicular to the template's vertical surface. Once the prostate volume and location have been confirmed on step section ultrasound planimetry, implant needles 16 are guided through the appropriate holes in the template 17 to the desired location within or around the prostate 10 in order to fulfill the brachytherapy plan.

However, as shown in FIG. 2A, the needle 16, as inserted through the needle guide 17, may not reach the target prostate area 10a, as it encounters the pubic arch 12. This is known as pubic arch interference, and may arise from patient positioning, patient anatomy or operator equipment orientation.

Pubic arch interference is frequently an insurmountable obstacle for even the most experienced brachytherapist. Needle displacement or blockage by bone can lead to significant loss of radiation dose coverage of the prostate. In one published series, Peschel from Yale University reported that 25% of his patients had pubic arch interference which disrupted the implant plan and drastically lowered disease-free survival rates at four years post implant (J Brachyther Intl 1998; 14: 197-8). Similarly, Wallner from Memorial Sloan-Kettering reported that approximately 20% of his patients were at risk for prostate gland underdosage because of bone interference (Wallner, J Urol 1991; 146:90-5).

Nearly all patients with localized prostate cancer could be candidates for integration of prostate brachytherapy into their treatment protocol. It is typically administered as the sole form of radiation therapy, or can be given in conjunction with external beam radiotherapy. However, some patients are precluded from undergoing prostate implantation for technical reasons. Chief among the contraindications is pubic arch interference.

Pubic arch interference is highly variable between patients, and is only loosely related to the size of the gland. Patients with a very small pelvic inlet may be difficult to implant despite a small gland volume. Conversely, patients with a large pelvic inlet may be easy to implant despite a large gland volume. The overriding issue is whether the pubic arch extends beyond the lateral and anterior margins of the prostate gland. If so, then it becomes extremely challenging, and sometimes impossible, to insert needles into the shielded regions of the prostate.

As stated above, pubic arch interference can be assessed via Computerized Tomography (CT) or ultrasound scan prior to the implant procedure in order to determine whether the pelvic bones might impede needle insertion. The largest prostate cross-section is overlaid on the narrowest section of pubic arch, and the overlap is measured. A rule of thumb is that if more than 25%, or one centimeter, of the prostate cross-section is blocked, the odds of achieving a successful implant are questionable (Bellon, IJROBP 1999; 43:579-81). The American Brachytherapy Society conducted a survey among brachytherapists and learned that prostate size greater than 60 grams was felt to be a relative contraindication to prostate brachytherapy alone (Nag, J Brachyther Int 1997; 13:243-51). It subsequently published consensus guidelines for clinicians recommending that implanting glands larger than 60 grams should not be attempted by novice brachytherapists because of the technical difficulties caused by pubic arch interference (Nag, IJROBP 1999; 44:789-99).

The seasoned brachytherapist can employ several maneuvers upon encountering pubic arch interference in order to skirt the pelvic bones and circumvent the pubic arch. This type of troubleshooting would permit implanting of the shielded portions of the prostate, thereby preserving the intended radiation dose distribution. The most basic maneuver, as shown in FIG. 2B involves withdrawing the needle and reinserting it into a neighboring hole in the needle guide 17. Here, the needle 16 reaches the prostate 10. Brachytherapy of the contacted portion of the prostate 10 is now possible, but the anterolateral portion of the prostate 10a, is left untreated or insufficiently treated.

Alternately, in this situation, the clinician can also slightly redirect the needle 16 using the bevel on the needle tip to cause the needle to diverge towards the desired location. If necessary, the needle 16 may be diverted after it has passed through the needle guide 17, but before it has entered the patient in a further effort to achieve the desired targeting. The needle tip 16a can be bent to deflect the needle towards the target location, but this can make it difficult to push the seed sources through, once the desired location is reached.

Repositioning the patient in an extended lithotomy posture, whereby the legs are drawn closer to the patient's head, can expand the space between the prostate and the pubic arch enough to allow accurate needle placement. The orientation of the template, in relation to the patient's perineum, can be modified by tilting the ultrasound support in an effort to bypass the obstructing bone. However, both of these methods may present severe discomfort or the potential for injury to the patient.

Finally, freehand needle placement can be attempted using various angles by removing the template grid. Again, this procedure still runs the risk of pubic arch interference.

Most brachytherapists have adopted the technique of modified peripheral seed source loading in order to minimize central high dose areas in the prostate. This has been done to protect the urethra. This style of seed implantation relies heavily on accurate seed placement in the outer portions of the prostate gland to generate the prescribed radiation dose. Therefore, avoidance of pubic arch interference is critical if one is to achieve a successful implant.

While pubic arch interference presents one of the greatest difficulties in brachytherapy, other factors also contribute to degradation of the intended dose during the implant procedure. These include patient motion, instability of the ultrasound stand or brace, poor ultrasound image quality, needle divergence, seed settling or migration, and misplacement of seeds in the bladder or rectum.

U.S. Pat. No. 2,269,963 (Wappler), U.S. Pat. No. 4,700,692 (Baumgartner), U.S. Pat. No. 5,242,373 (Scott), U.S. Pat. No. 5,860,909 (Mick), U.S. Pat. No. 5,928,130 (Schmidt), and U.S. Pat. No. 6,007,474 (Rydell) reflect devices that are employed to implant radioactive seeds into tissue. None addresses the problem of pubic arch interference. None of the implant needles currently available, including those described in U.S. Pat. Nos. 5,938,583 (Grimm) and 6,210,315 (Andrews), or those marketed by Mentor, Mick (MTP-1720-C, MTP-1820-C), Med-Tec (MT-BRACHYTHERAPY-5001-25, MT-BRACHYTHERAPY-5051-25), Best (Flexi-needle), Bard (BrachyStar®), or MD Tech offer a solution to the problem. The prostate stabilization needles in U.S. Pat. No. 4,799,495 (Hawkins) used during prostate brachytherapy to immobilize the gland do not help the brachytherapist avoid the pubic arch. Neither the real time brachytherapy spatial software registration and visualization system outlined in U.S. Pat. No. 6,129,670 (Burdette), nor the prostate brachytherapy software planning engine recently described in U.S. Pat. No. 6,200,255 (Yu), provides a solution to pubic arch interference despite a sophisticated approach to seed implantation. Finally, in U.S. Pat. No. 6,027,446 (Pathak), there has been devised a method for assessment of pubic arch interference, but has not offered a remedy.

There is a substance in current use in medicine which possesses properties that, when adapted to brachytherapy, may be exploited to overcome pubic arch interference. Nickel-titanium alloys, commonly known as Nitinol®, show a very pronounced shape memory and superelastic effect. Shape memory characteristics allow it to stay in a deformed shape until heated, whereupon it returns to its pre-deformed shape. For example, a surgical hook may be deformed into a straight configuration at room temperature and recover its hooked shape upon introduction to tissue, which is above room temperature. The superelastic characteristics of Nitinol® allow a hook to be constrained within a straight cannula during insertion into tissue, only to immediately regain its curved shape upon deployment into the tissue. Recovery of its original shape during unloading is the unique aspect of nickel-titanium alloys that is responsible for its integration into many medical inventions, eg. U.S. Pat. No. 5,000,912 (Bendel), U.S. Pat. No. 5,011,473 (Gatturna), U.S. Pat. No. 5,219,358 (Bendel), and U.S. Pat. No. 6,033,404 (Melzer).

SUMMARY

The systems, apparatus, components and methods disclosed herein improve on the conventional art, as they allow the clinician to circumvent the pubic arch in instances where it interferes with insertion of instrumentation into the prostate or periprostatic tissue. The systems, apparatus and components disclosed herein employ structures of nickel-titanium alloys for the purpose of skirting impediments to brachytherapy needle insertion by taking advantage of its shape memory and/or superelastic characteristics.

There is disclosed an improved brachytherapy implantation device and accompanying method, that is a combination instrument comprising a sleeve, a nickel-titanium needle, and a seed insertion stylet. The sleeve element has a slightly larger diameter than the nickel-titanium needle, and the nickel-titanium needle in turn has a slightly larger diameter than the seed insertion stylet. The needle and seed insertion stylet can be deployed from their sleeve, causing the needle to assume its prior shape as it is inserted into the prostate. The needle will thus circumvent an obstruction by arching around it. Upon withdrawal of the seed insertion stylet from the needle, a single seed or multiple seeds are entered into the needle at its hub end and propelled forward with the seed insertion stylet to the needle tip. As the needle and sleeve are withdrawn from the prostate, the stylet is held in position relative to the needle and sleeve, and the seed or seeds are deposited in the desired location beyond the pubic arch obstruction.

An embodiment disclosed is directed to a medical device having an elongated sleeve with a distal end and a proximal end, a needle slideable within the elongated sleeve, the needle including a distal segment, and at least a portion of the distal segment slideable beyond the distal end of the elongated sleeve. The needle is formed of a shape memory material, and the distal segment of the needle has a preformed shape trained into it, for example, a curved shape, such that it assumes the preformed shape upon being slid beyond the distal end of the elongated sleeve, when in the body.

Another embodiment disclosed is directed to a medical device having an elongated sleeve with a distal end and a proximal end. A leading member, for example, a needle with a central bore or a trocar, is slideable within the elongated sleeve. This leading member includes a distal segment, with at least a portion of a distal segment slideable beyond thee distal end of the elongated sleeve. The leading member is formed of a shape memory material, and the at least a portion of the distal segment of the leading member has a preformed shape trained into it, for example, a curved shape, such that it assumes the preformed shape upon being slid beyond the distal end of the elongated sleeve, when in the body.

Another embodiment is directed to a medical device having an elongated sleeve with a distal end and a proximal end, a trocar slideable within the elongated sleeve, the trocar including a distal segment, and at least a portion of the distal segment slideable beyond the distal end of the elongated sleeve. The trocar is formed of a shape memory material, and at least a portion of the distal segment of the trocar has a preformed shape trained into it, for example a curved shape, such that it assumes the preformed shape upon being slid beyond the distal end of the elongated sleeve, when in the body.

Another embodiment is directed to a method for treating at least a portion of the prostate, for example, the anterolateral portion obstructed by (typically behind) the pubic arch. The method involves providing an apparatus having an elongated sleeve with a distal end and a proximal end, a needle slideable within the elongated sleeve, the needle including a distal segment, at least a portion of the distal segment slideable beyond the distal end of the elongated sleeve; and the needle being formed of a shape memory material, with a curved shape preformed into at least the distal portion. The apparatus is then moved to a sufficient depth within the prostate in a direction from the perineum to the prostate, and at least a portion of the distal segment is extended beyond the distal end of the elongated sleeve to the desired site within the prostate, such that upon contact with the prostate tissue, the needle returns (e.g., curving) to its preformed shape. At least one treatment element, for example, a seed or a spacer, is guided through at least a portion of the needle to the desired site within the prostate.

Another embodiment is also directed to a method for treating at least a portion of the prostate, for example, the anterolateral portion obstructed by the pubic arch. The method involves providing an apparatus having an elongated sleeve with a distal end and a proximal end, a needle slidable within the elongated sleeve, the needle including a distal segment, at least a portion of the distal segment slideable beyond the distal end of the elongated sleeve, and the needle being formed of a shape memory material, with a curved shape preformed into at least the distal portion. At least one treatment element, for example, a seed or a spacer, is provided in the distal segment of the needle. The apparatus is moved to a sufficient depth within the prostate in a direction from the perineum to the prostate. At least a portion of the distal segment is extended beyond of the needle the distal end of the elongated sleeve to the desired site within the prostate, such that upon contact with the prostate tissue, the needle returns to its preformed shape. The at least one treatment element is then guided through at least a portion of the needle to the desired site within the prostate.

Another embodiment is directed to a method for treating at least a portion of the prostate, for example, the anterolateral portion obstructed by the pubic arch. The method involves providing an apparatus having an elongated sleeve with a distal end and a proximal end, a needle slideable within the elongated sleeve, the needle including a distal segment at a distal end of the needle, at least a portion of the distal segment slideable beyond the distal end of the elongated sleeve, and the needle being formed of a shape memory material, with a curved shape preformed into at least the distal portion. The apparatus is moved to a sufficient depth within the prostate in a direction from the perineum to the prostate. At least a portion of the distal segment of the needle is extended beyond the distal end of the elongated sleeve to the desired site within the prostate, such that upon contact with the prostate tissue, the needle returns to its preformed shape. The elongated sleeve is removed from the body. A sheath is then moved over the needle to a point proximate the distal end of the needle. The needle is removed from the body, and at least one treatment element, for example, a seed or a spacer, is guided through at least a portion of the sheath to the desired site within the prostate.

Another embodiment is directed to a method for treating at least a portion of the prostate, for example, the anterolateral portion obstructed by the pubic arch. The method involves providing an apparatus having an elongated sleeve with a distal end and a proximal end, a trocar slideable within the elongated sleeve, the trocar including a distal segment at a distal end of the trocar, at least a portion of the distal segment slideable beyond the distal end of the elongated sleeve, and the trocar being formed of a shape memory material, with a curved shape preformed into at least the distal portion. The apparatus is moved to a sufficient depth within the prostate in a direction from the perineum to the prostate. At least a portion of the distal segment of the trocar is extended beyond the distal end of the elongated sleeve to the desired site within the prostate, such that upon contact with the prostate tissue, the trocar returns to its preformed shape. The elongated sleeve is removed from the body. A sheath is moved over the trocar (for example, by sliding) to a point proximate the distal end of the trocar. The trocar is removed from the body, and at least one treatment element, for example, a seed or a spacer, is guided through at least a portion of the sheath to the desired site within the prostate.

Accordingly, several objects and advantages disclosed herein provide a means of avoiding pubic arch interference during prostate brachytherapy, to provide a radiopaque needle or trocar, for use with image-guidance during the brachytherapy procedure, to provide an MRI-compatible needle for use with MRI-guidance, to provide a deflectable implantation device which permits implementation of the brachytherapy dosimetry plan to avoid underdosing lateral aspects of the prostate and overdosing more central aspects of the prostate, and to provide a safe means of implanting prostates with larger volumes than are presently considered technically feasible. Still further objects and advantages will become apparent from a study of the following description and accompanying drawings.

BRIEF DESCRIPTION OF THE DRAWINGS

Attention is now directed to the drawing figures, where like numerals, or characters indicate corresponding or like components. In the drawings.

DETAILED DESCRIPTION OF THE DRAWINGS

Figure 3:
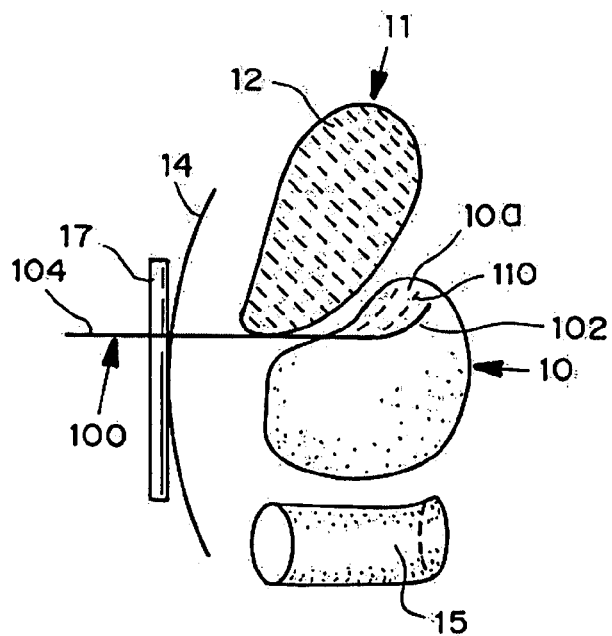
FIG. 3 is a schematic cross-sectional view of a disclosed embodiment in an exemplary operation in the body.

FIG. 3 shows the apparatus 100 disclosed herein in an exemplary operation (detailed below). Here, the apparatus 100 is such that the needle 102 at its distal end, extends beyond the sleeve 104, such that the portion 102a of the distal segment 102b (FIG. 4B) of the needle 102 beyond the sleeve 104 bends to its preformed or pretrained shape. This allows for treatment elements, for example, seeds 110 and spacers (or seeds 110 without spacers) to be deployed, for example adjacent one another and in rows (only one row shown for example only), in accordance with the operator's treatment protocol, in the anterolateral portion 10a of the prostate 10, through the needle 102, in accordance with standard brachytherapy procedures. A needle guide template 17 may be used for guiding the apparatus 100.

Figure 4A:
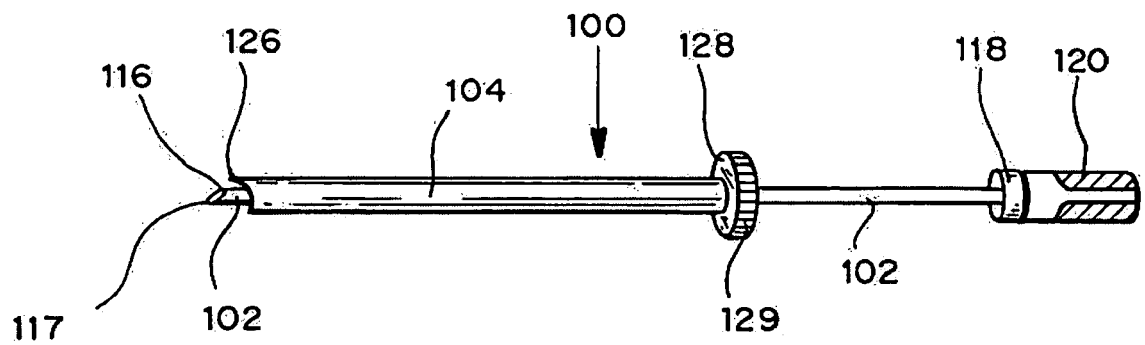
FIGS. 4A and 4B are side views of the embodiment of the apparatus disclosed in FIG. 3.
Figure 4B:
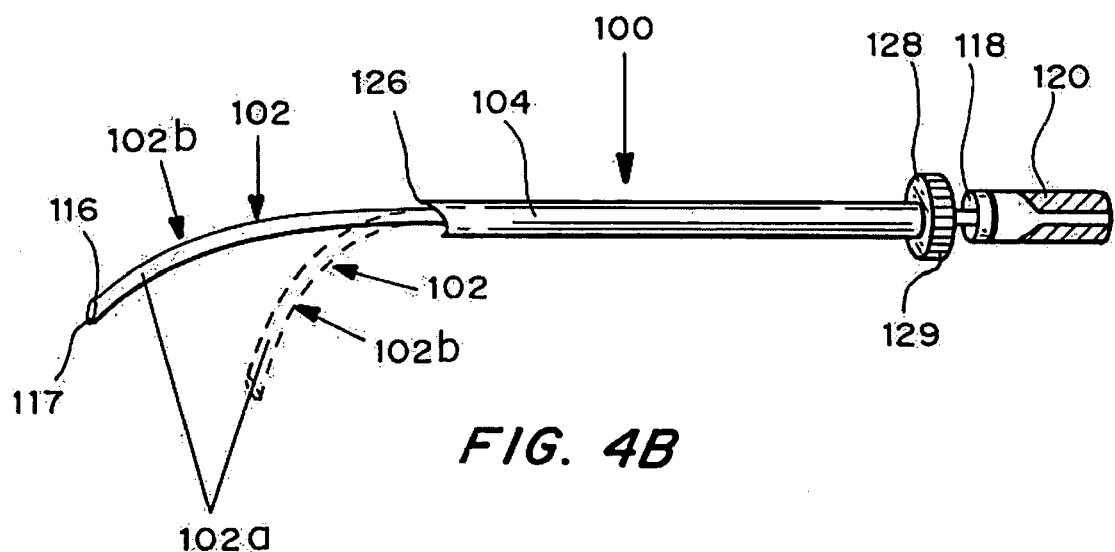

FIGS. 4A and 4B show the apparatus 100 prior to deployment. This apparatus 100 includes the needle 102, surrounded along a portion of its length by a sleeve 104.

Figure 5:
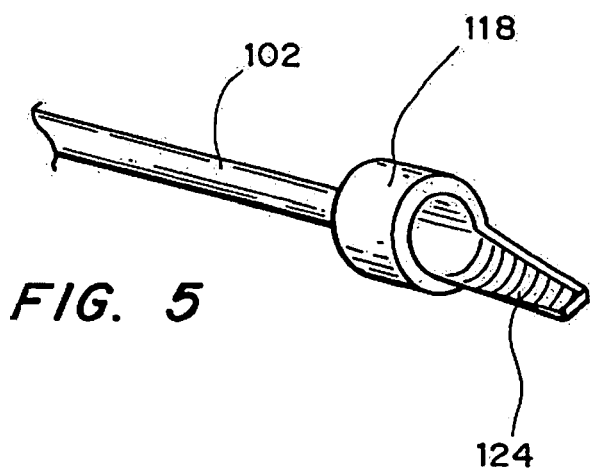
FIG. 5 is a perspective view of the hub portion of the needle.

The needle 102 terminates in a tip 116, typically a bevel 117 or a point, at one end, and in a hub 118 at the other end. This tip 116 can be, for example, echogenic. The hub 118 is dimensioned to receive a core 120 of a stylet 122 (FIG. 5), in a frictional engagement, such that the core 120 can be temporarily retained in the hub 118. The hub 118 is typically funnel-like in shape. It includes a grooved lip 124 (FIG. 6) on the side of the bevel 117, that coupled with the funnel-like shape facilitates loading of the needle 102 with seeds.

The sleeve 104 has a flat edged opening 126 at one end, and a collar 128, extending around it at the other end. The collar 128 typically includes ridges 129 to allow for ease in gripping of the sleeve 104.

Figure 6:
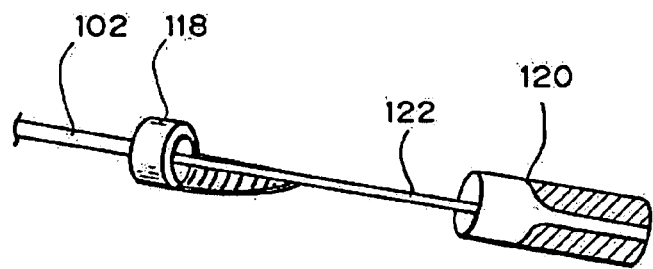
FIG. 6 is a perspective view of the stylet of the apparatus of FIG. 3.

Turning also to FIG. 6, the stylet 122 is dimensioned to extend through the needle 102 to at least the tip 116, and for example, to the point or bevel 117. The stylet 122 prevents the needle 102 from clogging during its deployment, as it prevents tissue from getting into the inner bore of the needle 102. This condition, where tissue gets into the inner bore of a needle as a result of its being open, is commonly known as "coring". The stylet 122 is typically in frictional contact with the inner walls of the bore of the needle 102, while being slidable within the needle 102. The needle 102 is typically in frictional contact with the inner walls of the sleeve 104, while being slideable within the sleeve 104.

The needle 102 is typically of a shape memory material such as nickel-titanium (Ni—Ti) or Nitinol®. Other suitable shape memory materials for the needle 102 can be, for example, Cu—Al—Ni, Cu—Zn—Al, Au—Cd, Mn—Cu, Ni—Mn—Ga. The needle 102 has a shape pretrained (preformed) into it, such that when it is in the body, it returns to this pretrained shape. Here for example, the needle 102 is trained to bend, and in particular, the portion of the needle 102a that extends from the sleeve 104 can bend to various curvatures (as illustrated in broken lines, and for example, rounded), as shown in FIG. 4B. This bending allows for accessing portions of the prostate 10 obstructed by (typically behind) the pubic arch 12, typically for seeding (as detailed herein).

The sleeve 104 is typically made of a surgical grade material, for use in the body. This material is typically rigid, so as to keep the portions of the needle 102 enclosed in the sleeve 104 in a straight or substantially straight orientation. The sleeve 104 can be made of, for example, a surgical grade stainless steel, or a Magnetic Resonance Imaging (MRI) compatible material such as titanium, polymers, non-ferromagnetic alloys (e.g., INCONEL® and HASTELLOY®) or a material that incorporates nanotechnology, such as with carbon based nanotubes. The sleeve 104 can also be made from polymeric materials, for example, polyetheretherketone, such as PEEK®. The collar 126 is typically made of the same materials as the sleeve 104 and joined thereto by conventional materials joining techniques.

The stylet 122 is typically flexible, so as to bend with the portion of the needle 102 that is extended out of the sleeve 104. The stylet 122 is for example, made of the materials used for the sleeve 104.

Figure 1:
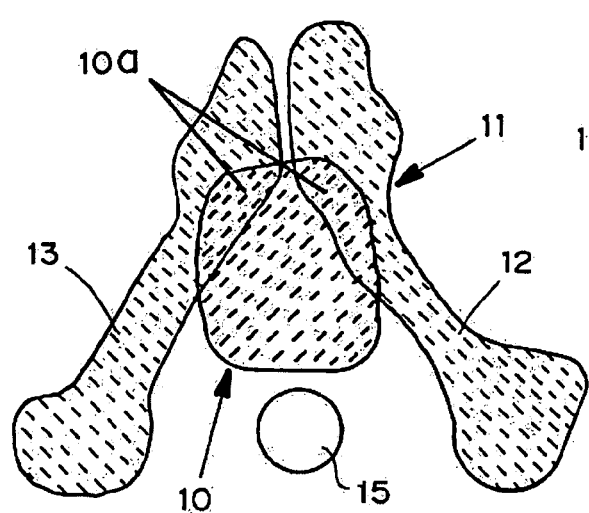
FIG. 1 is a schematic view, from the perineum, of the prostate in relation to the pubic arch and the rectum.
Figure 2A:
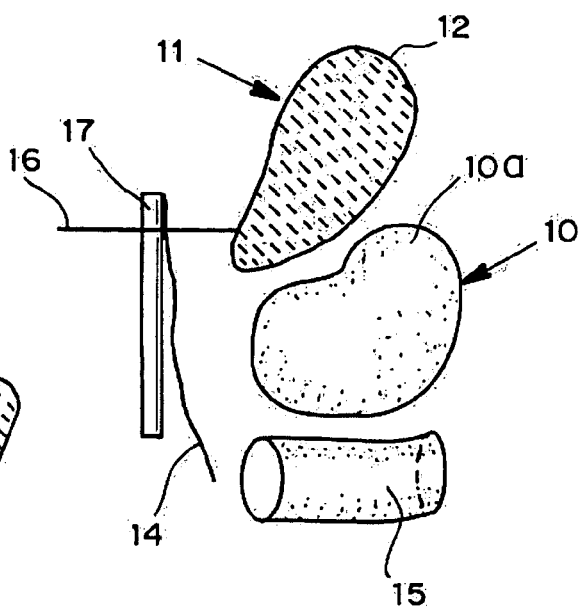
FIG. 2A is a schematic cross-sectional view of the prostate and pubic arch of FIG. 1 with an implant needle traversing the template needle guide.
Figure 2B:
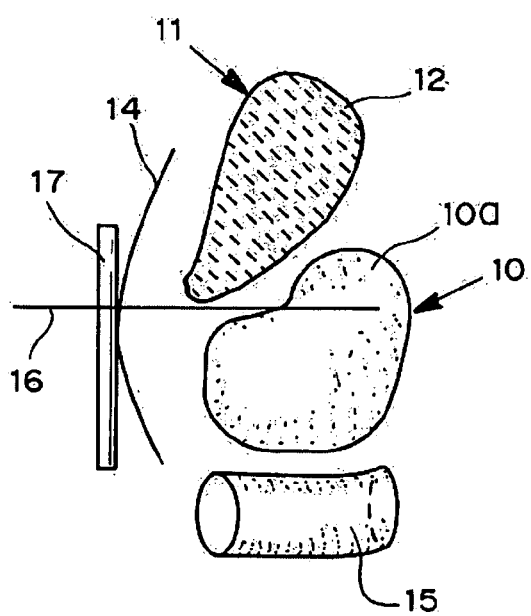
FIG. 2B is a schematic cross-sectional view of the prostate and pubic arch of FIGS. 1 and 2A with the implant needle traversing the template needle guide through a different hole in the template.

Reference will be made to FIGS. 3-6 to describe an exemplary operation for the apparatus 100. Initially, a viewing device, for example, an ultrasound or MRI probe, is placed into the rectum 15 (FIG. 1) for guiding the apparatus 100. The apparatus 100, as shown in FIGS. 4A, 4B, 5 and 6 is typically placed through a template or needle guide 17, and moved toward the prostate 10, as shown in FIG. 3. During this advancement, the needle 102 is in a position where its tip 116, is proximate the sleeve opening 126 and the end of the stylet 122 is proximate to the needle tip 116, sitting slightly behind (proximal to) the bevel 117 in the needle bore (so the needle tip 116, in particular, the bevel 117 acts as the cutting edge with the stylet 122 deflecting tissue from the needle bore). The apparatus 100 is advanced to an appropriate depth, with its position confirmed by tactile factors felt by the clinician upon attaining penetration depths, coupled with imaging data from the ultrasound or MRI probe.

The apparatus 100 may, for example, have a needle 102 that is 18 gauge, while the sleeve 104 is of a 17 gauge. This allows the apparatus 100 to be of a suitable gauge for seed (and spacers, if necessary) passage, while allowing it to be used with standard templates or needle guides, whose openings are typically configured for accommodating 17 gauge instruments.

Once the apparatus 100 is at this position, such that the anterolateral portion 10a of the prostate 10 is reachable by the needle 102, a portion 102a of the distal segment 102b of the needle 102, and corresponding portion of the stylet 122, are extended beyond the sleeve 104. The needle 102 has been previously oriented by the clinician, typically by rotating it at the hub 118, such that it upon its release from the sleeve 104, it bends, in accordance with the pretrained shape, to access the anterolateral portion 10a of the prostate 10.

With access now attained, the stylet 122 is removed, typically by pulling on the core 120. Radioactive seeds 110 and spacers if desired, can now be loaded into the needle 102, through the hub 118. Seeds can be for example, capsule-like in shape, typically with a capsule of titanium or stainless steel, for encapsulating a radioisotope. These seeds 110 can be for example, I-125 or Pd-103 brachytherapy seeds, or other conventional brachytherapy seeds. Other radioactive seeds, suitable for use here, can be, for example, those detailed in PCT Patent Application PCT/US01/43517, entitled: Polymeric Imagable Brachytherapy Seed, this PCT patent application incorporated by reference herein. The capsule of these seeds is made of a biocompatible substance, such as polymeric materials, and is tightly sealed to prevent leaching of the radioisotope. These aforementioned seeds for example, have diameters of about 0.8 mm and a length of about 4.5 mm, so as to fit in the bore of an 18 gauge needle.

Exemplary radioactive seeds include Symmetra® I-125 (Bebig GmbH, Germany), IoGold™ I-125 and Pd-103 (North American Scientific, Chatsworth, Calif.), Best® I-125 and Best® Pd-103 (Best Industries, Springfield, Va.), Brachyseed® I-125 (Draximage, Inc., Canada), Intersource® Pd-103 (International Brachytherapy, Belgium), Oncoseed® I-125 (Nykomed Amersham, UK) STM 1250 I-125 (Sourcetech Medical, Carol Stream, Ill.), Pharmaseed® I-125 (Syncor, Woodland Hills, Calif.), Prostaseed® I-125 (Urocor, Oklahoma City, Okla.) and I-plant® I-125 (Implant Sciences Corporation, Wakefield, Mass.).

Alternately, the seeds can be non-radioactive. These non-radioactive seeds would typically be impregnated with drugs or the like.

Spacers can be, for example, those described in PCT Patent Application PCT/US01/43517, that is incorporated by reference herein. Spacers, can be, for example, of a biocompatible material that can be used to join two brachytherapy seeds. The biocompatible material can be either biodegradable or non-biodegradable. These exemplary spacers can be made of catgut or a like material. For example, Ethicon, Inc. (Cincinnati, Ohio) manufactures the PG 910 non-sterile autoclavable spacer for Indigo (Cincinnati, Ohio) that is sold in conjunction with an Express Seed Cartridge. In addition, Medical Device Technologies, Inc. (Gainesville, Fla.) distributes a presterilized, 5.5 mm (in length) absorbable pre-cut spacer that is made of collagen (LOOK®, Model No. 1514b). The spacers can also be of radiopaque materials.

The stylet 122 can now be inserted back into the needle 102, to push the seeds 110, and spacers if desired, for their placement at the desired destination. Alternately, another stylet or blunt obterator can replace the stylet 122 on reinsertion into the needle 102 and pushing and placement of the seeds 110 (and spacers). This seeding step can be repeated for as long as necessary.

Alternately, seeds (and spacers if desired) can be preloaded in the apparatus 100. Here, a seed, of the desired amount of seeds and spacers (if desired), would be placed into the needle 102, so as to be at the needle tip 116. This seed serves to keep the needle bore closed to prevent coring (as detailed above). The stylet 122 or a blunt obterator would be in the needle 102 immediately following (or proximal) the seed(s) (and spacers, if necessary). All other needle positioning and seed (and spacer) deployment, would be in accordance with the procedure detailed above.

Alternately, the aforementioned process can modified slightly for high dose rate (HDR) brachytherapy. In this process, once the needle 102 has accessed the anterolateral portion of the prostate, an encapsulated radioactive source, for example, an iridium-192 seed, may be driven through the needle 102 to the tip 116 with a mechanized cable or line. The seed would be permitted to dwell for a designated time period, and then it would be retrieved by the same cable or line (typically by being attached thereto).

Alternately, the guidance of the needle 102, sleeve 104, and stylet 122, can be by external imaging, for example CT or MRI. It can also be by techniques, such as Fluoroscopy (as many materials for at least the needle 102, and sleeve 104 are radiopaque by their general nature, with other materials listed above for the needle 102 and sleeve 104 easily modified to be radiopaque). The needle 102 can also be guided by use of a look-up table or by a software program, in accordance with U.S. Pat. No. 6,368,331 (Front, et al.), this document incorporated by reference herein. Additionally, prior to entry into the body, the needle 102 can be preheated, should the material of the needle be such that this external heating is required in addition to body heat to activate the preformed (pretrained) configuration of the needle 102.

Figure 7A:
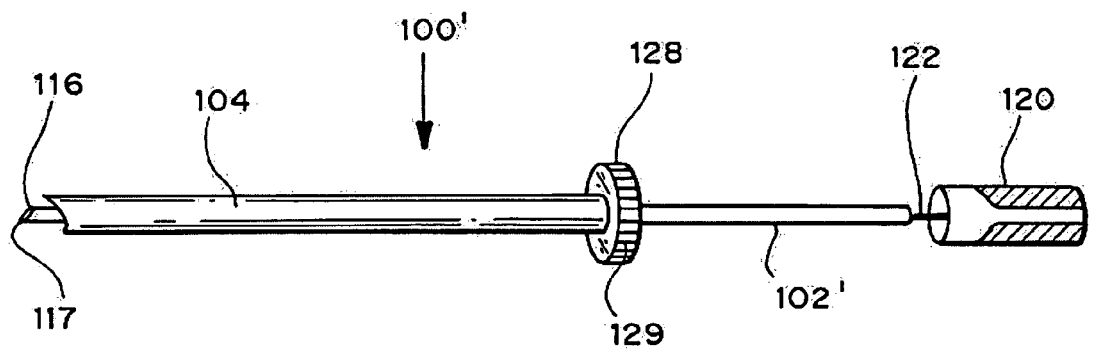
FIGS. 7A and 7B are side views of a second embodiment of an apparatus.
Figure 7B:
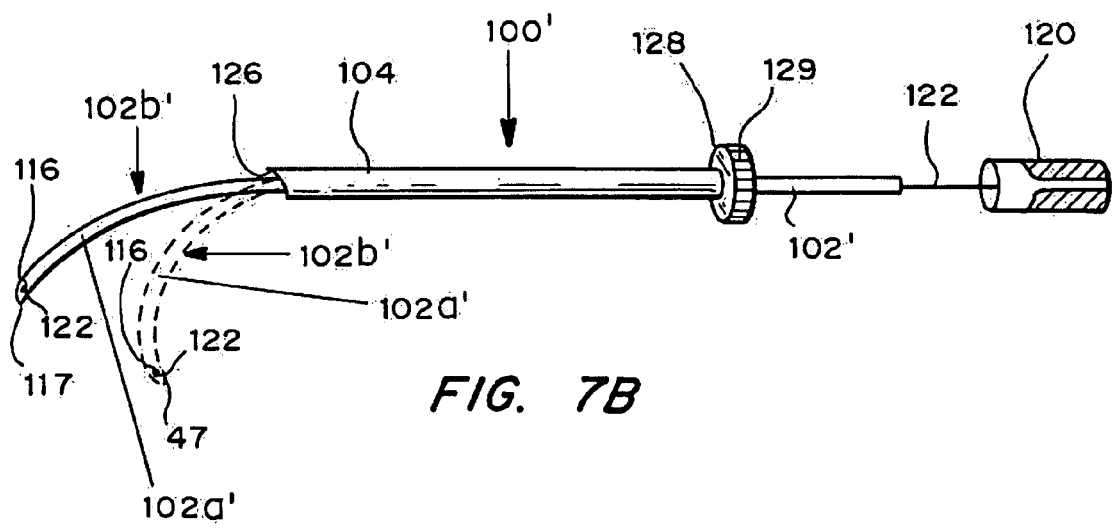

FIGS. 7A and 7B detail an alternate embodiment apparatus 100' of the apparatus 100 detailed above. Here, the apparatus 100' is similar in construction, arrangement and materials to apparatus 100, with identically numbered components, except where indicated.

The apparatus 100' includes a needle 102' similar in all aspects to needle 102, except that it either has a detachable, for example, a clip-on hub (not shown), or lacks a hub. This is because a sheath 150 (FIGS. 8A-8C) is configured for being placed over the needle 102' once it is deployed to reach the target area of the prostate. A sleeve 104 extends over the needle 102', with a stylet 122 extending through the needle 102, so as to prevent coring (as detailed above). A portion 102a' of the distal segment 102b' of the needle 102' extends beyond the sleeve 104, so as to curve in order to reach desired portions, for example, the anterolateral portion 10a of the prostate 10.

Figure 8A:
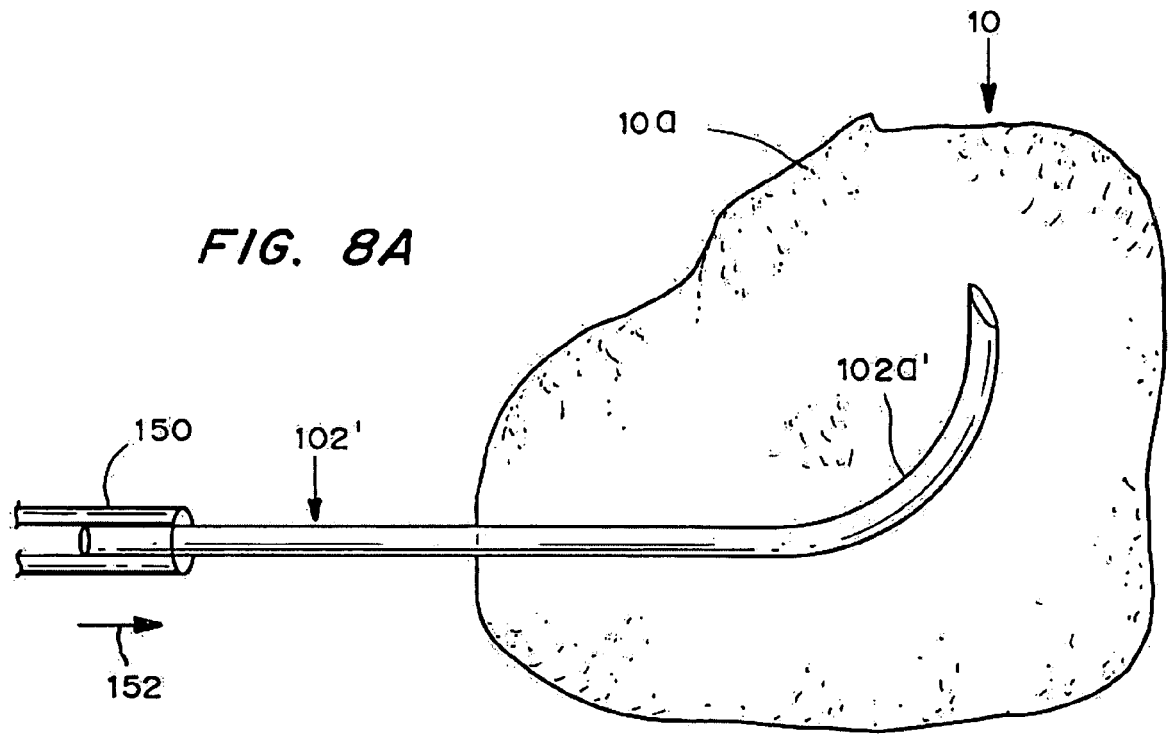
FIGS. 8A-8C are diagrams detailing the operation of the apparatus of FIGS. 7A and 7B.
Figure 8B:
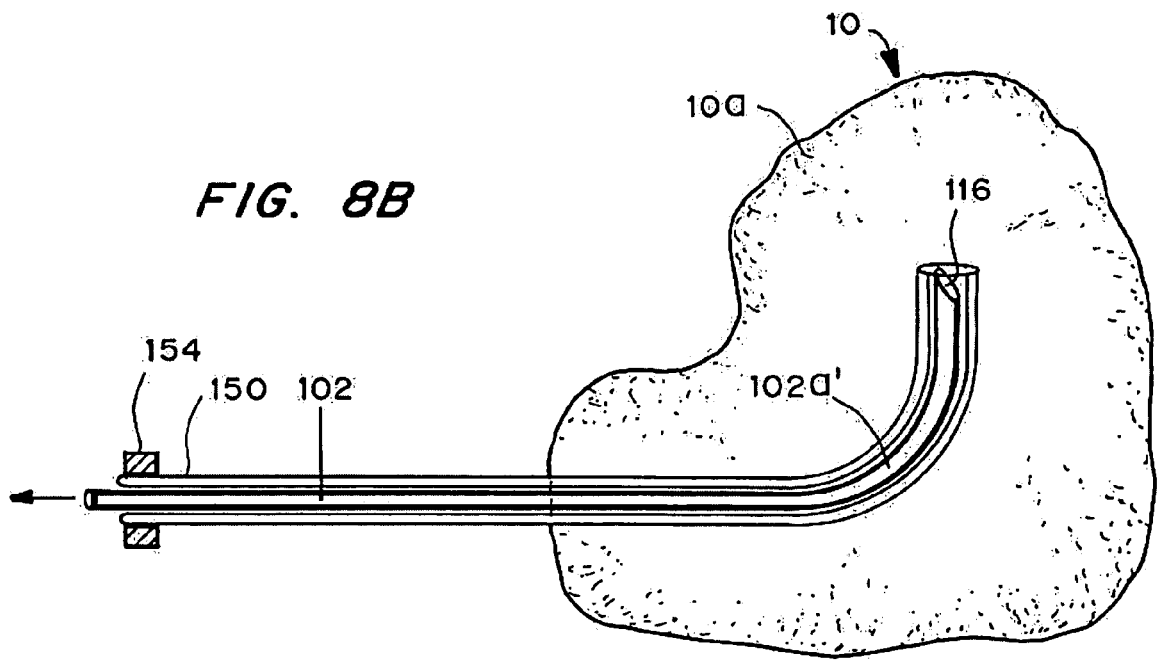
Figure 8C:
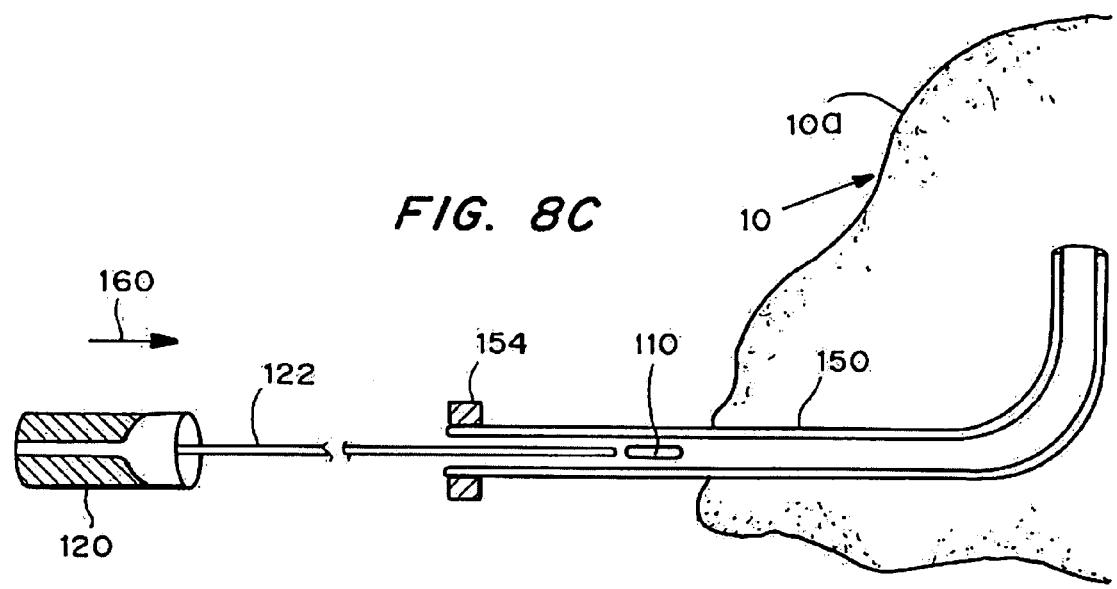

Turning also to FIGS. 8A-8C, an exemplary operation of the apparatus 100' is detailed. Deployment of the apparatus 100' under guidance of the clinician, through tactile factors (detailed above) and imaging data from the ultrasound or MRI probes, or external guidance, is similar to that for apparatus 100 detailed above. During this advancement, the needle 102' is in a position where its tip 116, is proximate the sleeve opening 126 and the end of the stylet 122 is proximate to the needle tip 116, similar to that for the apparatus 100 above. Once the desired position for the sleeve 104 is attained, a portion 102a' of the needle 102', with the corresponding portion of the stylet 122, is moved beyond the sleeve 104, with the needle 102' having the position of the broken line portion of FIG. 7B.

With the needle 102' in its desired position at the desired depth, the stylet 122 is removed, by pulling it out of the needle 102'. The sleeve 104 is then removed, pulling it out of the body. Alternately, the sleeve 104 and stylet 122 can be removed together.

The sheath 150, typically made of a flexible polymer, that is, for example, MRI compatible, is then moved over the needle 102', in the direction of the arrow 152, as shown in FIG. 8A. The sheath 150 typically includes a hub 154 (FIGS. 8B and 8C) at its proximal end to allow for easier gripping and retention by the clinician or operator. Movement of the sheath 150 continues until it is proximate the needle tip 116, as shown in FIG. 8B. The needle 102' is then removed from the sheath 150 (in the direction of the arrow 158), leaving an open path to the prostate 10, in particular, the anterolateral portion 10a thereof. The sheath 150 can also be of radiopaque polymers or radiopaque portions thereof, or of materials modified to be radiopaque.

As shown in FIG. 8C, a seed 110 (as detailed above) is placed into the sheath 150 and pushed toward the prostate 10 by a stylet 122 or blunt obturator (in the direction of the arrow 160). Pushing continues until the seed 110 is properly positioned in the prostate 10. While a single seed is shown, this is exemplary only, as the seed could be replaced by multiple seeds and spacers (as detailed above) if desired.

The procedure can be repeated as long as desired. With the procedure complete, the sheath 150 can be withdrawn from the body.

In this embodiment, the needle 102', for example, may be less than 18 gauge, as it serves to create a pathway to the anterolateral portion 10a of the prostate 10. For example, the sleeve 104 would be of an inner diameter (bore) gauge greater than the needle, but not greater than 17 gauge, so as to fit within openings on a conventional template or needle guide (typically configured for accommodating 17 gauge instruments, as detailed above). The sheath 150, for example, could be 18 gauge or greater in order to accommodate seeds (and spacers, if necessary) while being able to easily slide over the needle 102'.

Alternately, the apparatus 100' could be used in High Dose Rate (HDR) Brachytherapy. The process would be similar to that detailed for apparatus 100, above, except that the encapsulated radioactive source would be driven down and retrieved through the sheath 150, instead of the needle 102.

Figure 9A:
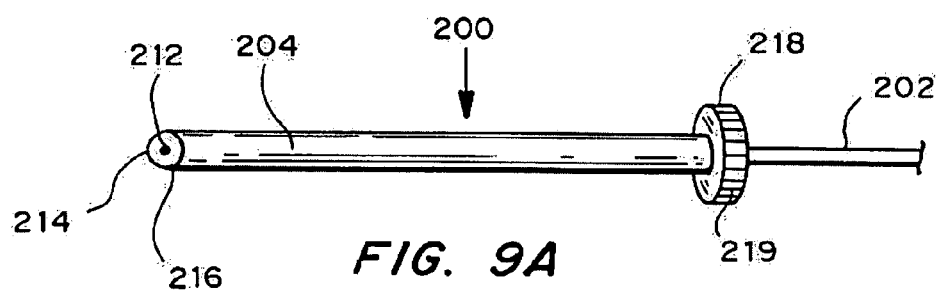
FIGS. 9A and 9B are side views of a third embodiment of an apparatus.
Figure 9B:
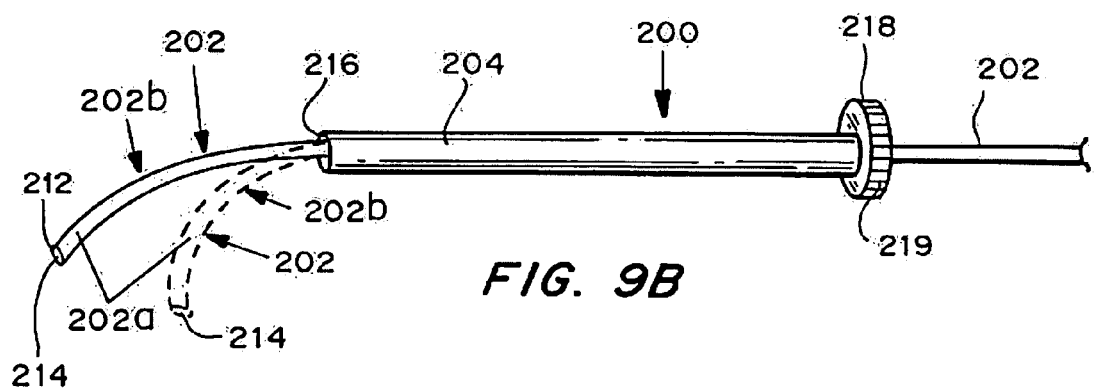

FIGS. 9A and 9B show a third apparatus 200. This apparatus 200 includes a trocar 202 and a cannula 204. The trocar 202 and cannula 204 are dimensioned such that the trocar 202 can slide within the cannula 204, such that a portion 202a of a distal segment 202b of the trocar 202, can be extended beyond the cannula 204, in order that it be deployed to the desired position (as detailed above).

The trocar 202 is a solid member, with a tip 212, for example, terminating in a point 214. Similar to the needle tip 116, detailed above, this tip 212 can be echogenic. By being a solid member, this prevents the cannula 204 from clogging during its deployment, as it prevents tissue from getting into the inner bore of the cannula 204, or "coring". The trocar 202 is typically of a shape memory material such as nickel-titanium or Nitinol® (or any of the other materials listed for the needle 102 above), with a shape, for example, a curvature (for example, rounded), pretrained (preformed) into it (as shown by broken lines in FIG. 9B). This way, when the trocar 202 is in the body, the portion 202a extended beyond the cannula 204 returns to this pretrained shape. This bending allows for accessing portions of the prostate 10 behind the pubic arch 12, typically for seeding (as detailed herein).

The cannula 204 is similar to sleeve 104 above, in that it has a flat edged opening 216 at one end, and a collar 218, extending around it at the other end. The collar 218 typically includes ridges 219 to allow for ease in gripping of the sleeve 204. The cannula 204 is of a material that is typically rigid, so as to keep the portions of the trocar 202 enclosed therein, in a straight or substantially straight orientation.

The cannula 204 is typically made of a surgical grade material, for use in the body. This material is typically rigid, so as to keep the portions of the trocar 202 enclosed in the cannula 204 in a straight or substantially straight orientation. The cannula 204 can be made of, for example, a surgical grade stainless steel, or a Magnetic Resonance Imaging (MRI) compatible material such as titanium, polymers, non-ferromagnetic alloys (e.g., INCONEL® and HASTELLOY®) or a material that incorporates nanotechnology, such as with carbon based nanotubes. The cannula 204 can also be made from polymeric materials, for example, polyetheretherketone, such as PEEK®. The collar 218 is typically made of the same materials as the cannula 204 and joined thereto by conventional materials joining techniques.

Figure 10A:
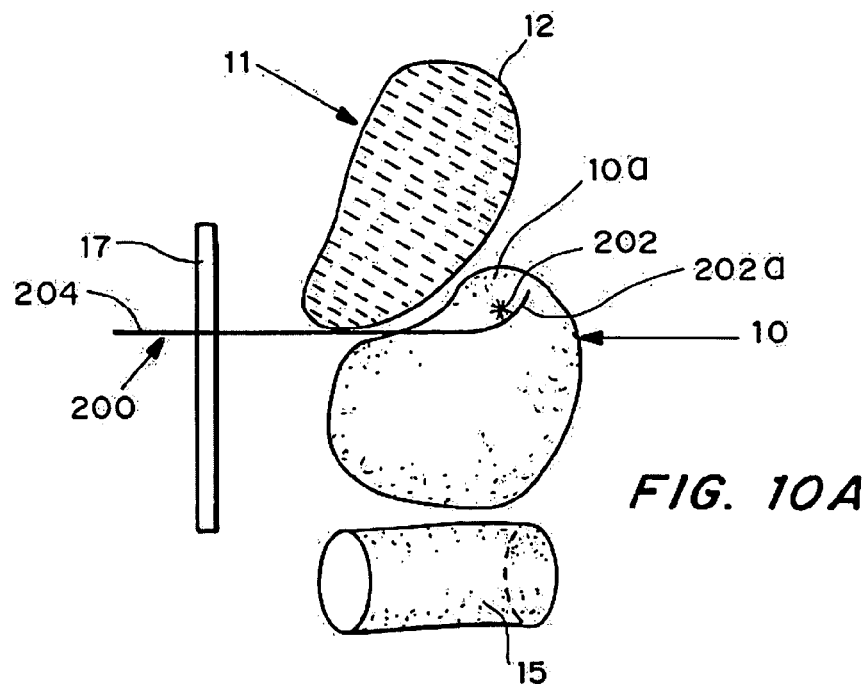
FIGS. 10A-10F are diagrams showing the operation of the apparatus of FIGS. 9A and 9B.
Figure 10B:
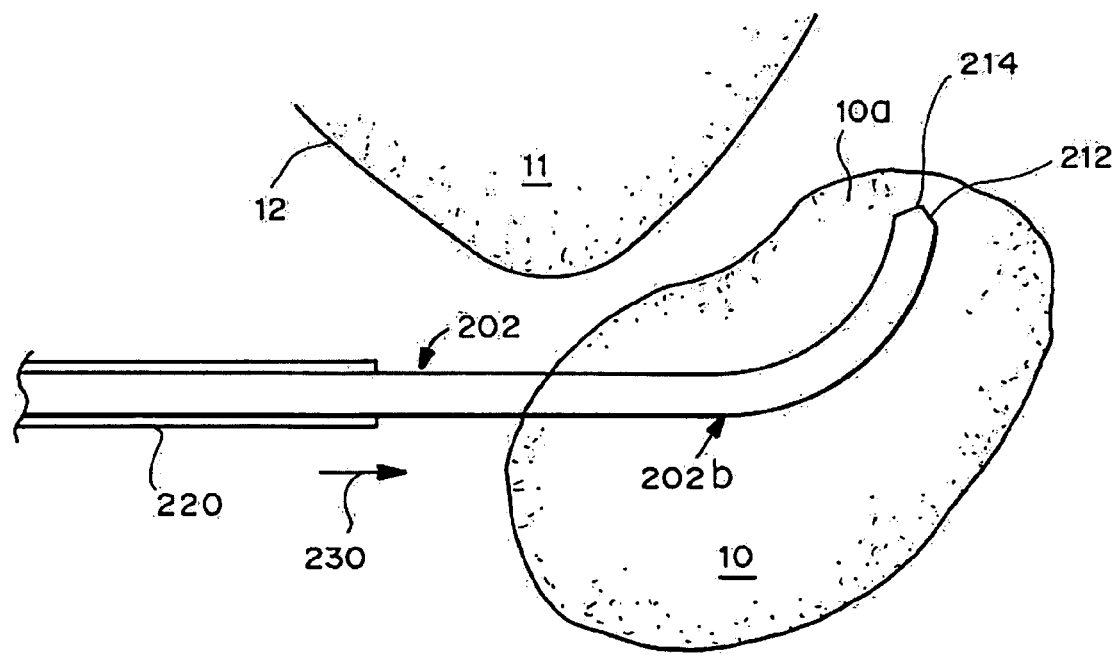
Figure 10C:
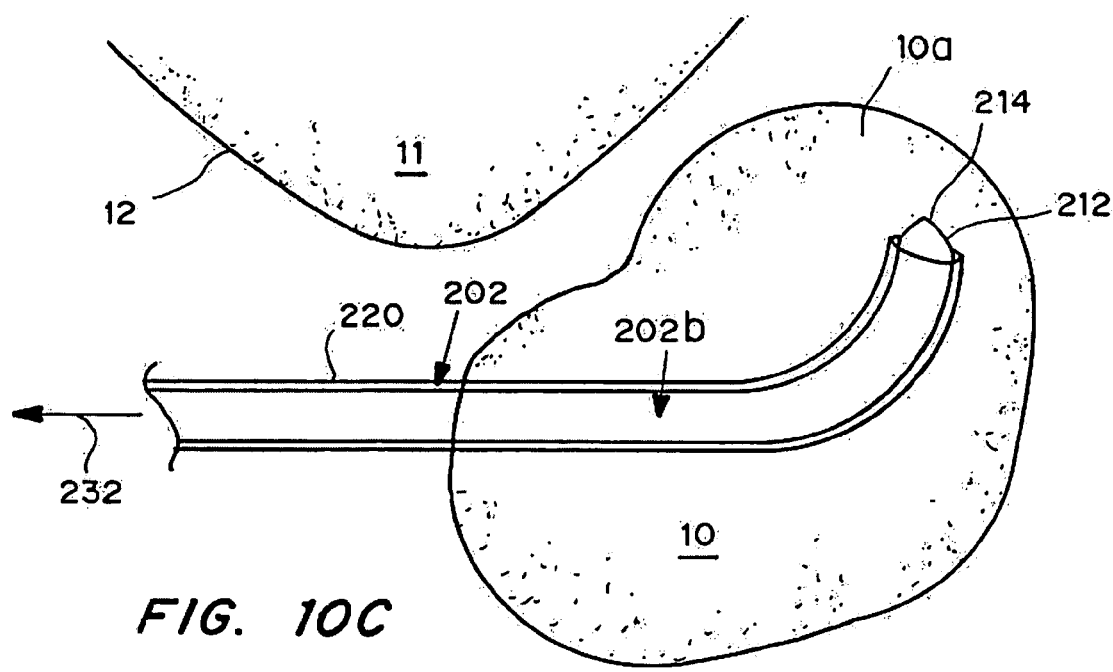
Figure 10D:
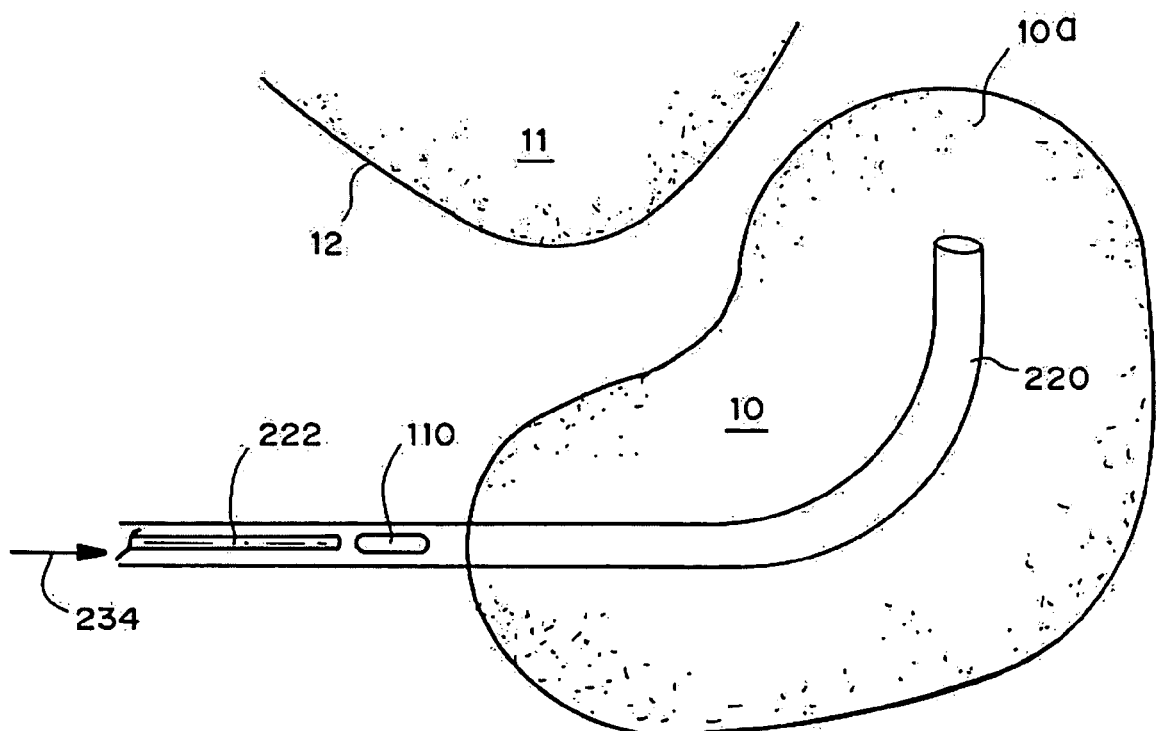
Figure 10E:
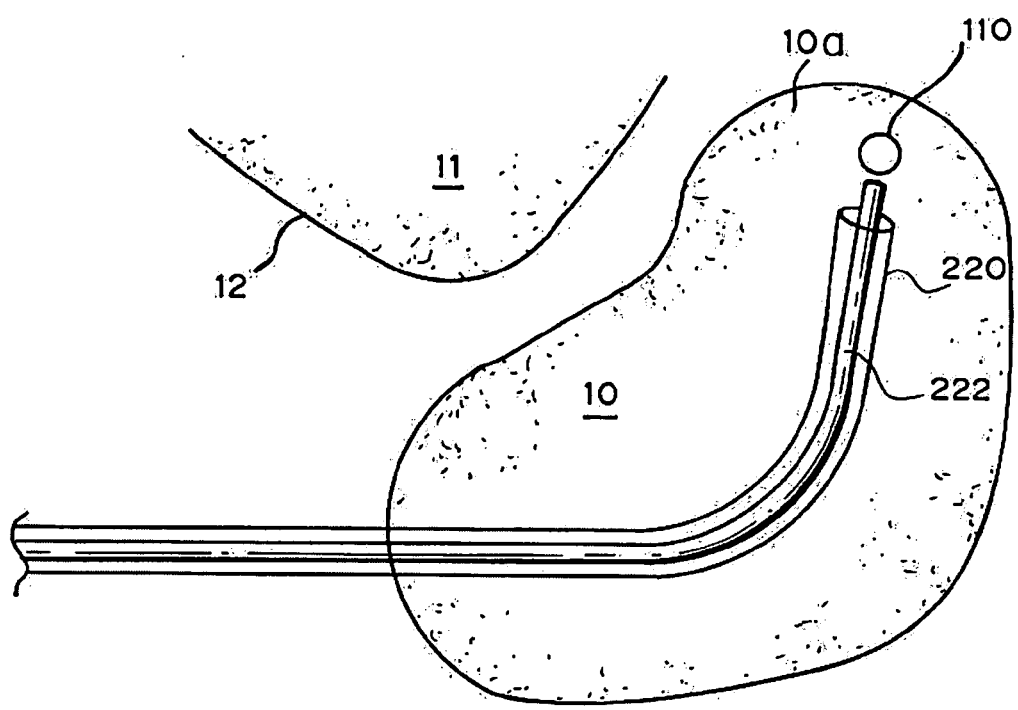

The apparatus 200 also includes a sheath 220 (FIGS. 10B-10E) and a stylet 222 (FIGS. 10D and 10E). The sheath 220 is typically a flexible sheath, similar to the sheath 150 detailed above, and is dimensioned to slide over the trocar 202, as it is placed over the trocar 202. The stylet 222 includes a hub 224, and is similar to the stylet 122 detailed above.

Turning now to FIGS. 10A-10F, an exemplary operation of the apparatus 200 is now described. Initially, a viewing device, for example, an ultrasound or MRI probe, is placed into the rectum 15 (FIG. 10A) for guiding the apparatus 200. Turning to FIG. 10A, the apparatus 200, is typically placed through a template or needle guide 17, and moved toward the prostate 10. The apparatus 200 is advanced to an appropriate depth, with its position confirmed by tactile factors felt by the clinician upon attaining penetration depths, coupled with imaging data from the ultrasound or MRI probe. During this advancement, the trocar 202' is in a position where its tip 214, is proximate the sleeve opening 216.

Once the apparatus 200 is at this point, a portion 202a of the trocar 202 is extended beyond the cannula 204. The trocar 202 has been previously oriented by the clinician, typically by rotating it, such that it upon its release from the cannula 204, it bends, in accordance with the pretrained (preformed) shape, to reach the anterolateral portion 10a of the prostate 10.

With the anteriorlateral portion 10a of the prostate 10 reached, the cannula 204 is removed from the body. The flexible sheath 220 is advanced over the trocar 202 to its tip 214, in the direction of the arrow 230, as shown in FIG. 10B. Advancement of the sheath 220 continues until it reaches the tip 212 of the trocar 202, as shown in FIG. 10C. The trocar 202 is then removed from the flexible sheath 220, by being slid out of the sheath 226 in a direction away from the body, in accordance with the arrow 232.

The apparatus 200 may, for example, have a trocar 202 of an 18 gauge size, while the sleeve 204 is of a 17 gauge size. This allows the for the sheath 220 to be of, for example, a 17 gauge, and thus a suitable gauge for seed (and spacers, if necessary) passage. Additionally, all instrumentation can be used with standard templates or needle guides, whose openings are typically configured for accommodating 17 gauge instruments (detailed above).

Figure 10F:
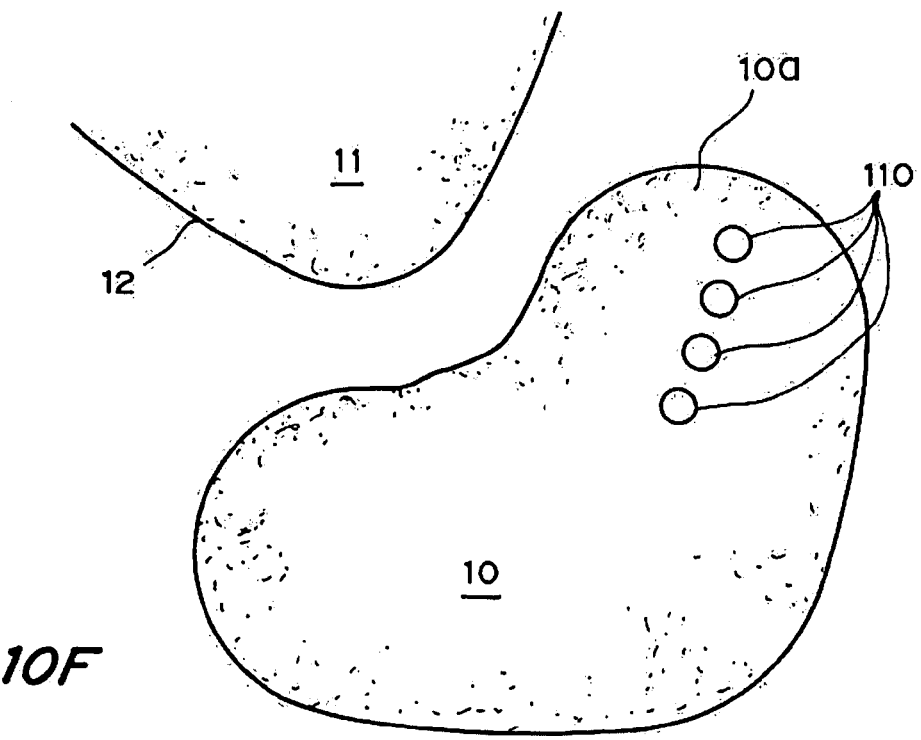

In FIG. 10D, with access now to the anterolateral portion 10a of the prostate 10 attained, radioactive seeds 110 (as detailed above) and spacers (as detailed above) if desired (one seed 110 shown as representative of seeds and spacers, if desired), can now be loaded into the sheath 220. The stylet 222 can now be placed into the sheath 220, and moved forward in the direction of the arrow 234. This forward movement moves the seeds 110 forward in the sheath 220, for their placement in the anteriorlateral portion 10a of the prostate 10, as detailed for apparatus 100 above, as shown in FIG. 10E. This seeding step can be repeated for as long as necessary. Once seeding is complete, as shown in FIG. 10F, the sheath 220 is removed, leaving the seeds 110 in place in the prostate 10, here the anterolateral portion 10a.

Alternately, the apparatus 200 could be used in High Dose Rate (HDR) Brachytherapy. The process would be similar to that detailed for apparatus 100, 100' above, except that the encapsulated radioactive source would be driven down and retrieved through the sheath 220, instead of the needle 102, and sheath 150, respectively.

Alternately, the guidance of the trocar 202, sleeve 204, and sheath 220, can be by external imaging, for example CT or MRI. It can also be by techniques, such as Fluoroscopy (as many materials for at least the trocar 202 and sleeve 204 are by their general nature radiopaque, with other materials listed above for the trocar 202 and sleeve 204 easily modified to be radiopaque), as detailed for the apparatus 100 above. The trocar 202 can also be guided by use of a look-up table or by a software program, in accordance with U.S. Pat. No. 6,368,331 (Front, et al.), as detailed for the apparatus 100 above, Additionally, prior to entry into the body, the trocar 202 can be preheated, should the material of the trocar be such that this external heating is required in addition to body heat to activate the preformed (pretrained) configuration of the trocar 102.

While the apparatus 100, 100' and 200 above have been described in association with brachytherapy procedures, this is exemplary only. The apparatus 100, 100' and 200 could be used in any procedure, where it is necessary to bypass bone, or other tissue masses (hard or soft tissue), organs, glands, or the like that may be in a the direct path of an instrument, to access and/or treat the desired treatment site behind the bypassed bone, tissue mass, organ, gland or the like. While exemplary treatments with treatment elements such as seeds, with and without spacers has been described, other treatment elements, for example, those detailed in PCT Patent Application PCT/US01/43517, could also be employed with the apparatus 100, 100' and 200, in similar manners.

While preferred embodiments of systems, apparatus, components and methods, have been described above, the description of the systems, apparatus, components and methods above is exemplary only. Those skilled in the art will recognize, or be able to ascertain using no more than routine experimentation, many equivalents to the specific embodiments of the invention described herein. Such equivalents are intended to be encompassed by the following claims.

What is claimed is:

1. A medical device comprising:
   an elongated sleeve with a distal end and a proximal end wherein the sleeve is formed of
   a rigid material;
   a trocar slidable within the elongated sleeve, the trocar including a distal segment, at least a portion of the distal segment slideable beyond the distal end of the elongated sleeve;
   wherein the trocar is solid and is formed of a shape memory material; and
   the at least a portion of the distal segment of the trocar having a preformed shape trained into it such that is assumes the preformed shape upon being slid beyond the distal end of the elongated sleeve in the body.

2. The device of claim 1, wherein the preformed shape is curved.

3. The device of claim 2, wherein the shape memory material includes a nickel-titaniun alloy.

4. The device of claim 1, wherein the trocar is 17 or 18 gauge.

5. The device of claim 1, additionally comprising a sheath configured for sliding over the trocar.

6. The device of claim 5, wherein the sheath includes an inner bore dimensioned to accommodate the passage of at least one brachytherapy seed therethrough.

7. The device of claim 6, wherein the inner bore is dimensioned to accommodate I-125 or Pd-103 brachytherapy seeds.

8. The device of claim 5, wherein the sheath is of a flexible material.

9. A method for treating at least a portion of the prostate comprising:
   a) providing an apparatus comprising:
      an elongated sleeve with a distal end and a proximal end;
      a trocar slidable within the elongated sleeve, the trocar including a distal segment at a distal end of the trocar, at least a portion of the distal segment slideable beyond the distal end of the elongated sleeve; and
      the trocar being formed of a shape memory material, with a curved shape preformed into at least the distal portion;
   b) moving the apparatus to a sufficient depth within the prostate in a direction from the perineum to the prostate;
   c) extending at least a portion of the distal segment of the trocar beyond the distal end of the elongated sleeve to the desired site within the prostate, such that upon contact with the prostate tissue, the trocar returns to its preformed shape;
   d) removing the elongated sleeve from the body;
   e) moving a sheath over the trocar to a point proximate the distal end of the trocar;
   f) removing the trocar from the body; and
   g) guiding at least one treatment element through at least a portion of the sheath to the desired site within the prostate.

10. The method of claim 9, wherein a moving the apparatus to a sufficient depth within the prostate includes moving the apparatus to a point at or beyond the pubic arch.

11. The method of claim 10, additionally comprising, orienting the trocar such that the trocar returns to its preformed shape at the anterolateral portion of the prostate.

12. The method of claim 9, wherein step (g) additionally comprises:
   placing the at least one treatment element into the sheath; and pushing the at least one treatment element through the sheath to the desired site within the prostate by inserting an instrument into the sheath.

13. The method of claim 12, wherein the at least one treatment element is at least one seed.

14. The method of claim 12, wherein the at least one treatment element is at least one spacer.

* * * * *